(12) United States Patent
Teng

(10) Patent No.: US 7,182,598 B2
(45) Date of Patent: Feb. 27, 2007

(54) DENTAL BITE CONFIGURATION RECORDING DEVICE

(76) Inventor: Kuo-Chi Teng, 13 F, No. 7, Lane 290, Bei-Tung Road, Taichung City (TW)

( * ) Notice: Subject to any disclaimer, the term of this patent is extended or adjusted under 35 U.S.C. 154(b) by 231 days.

(21) Appl. No.: 10/962,489

(22) Filed: Oct. 13, 2004

(65) Prior Publication Data

US 2005/0084817 A1    Apr. 21, 2005

(30) Foreign Application Priority Data

Oct. 16, 2003   (TW)   .............................. 92128765 A

(51) Int. Cl.
*A61C 19/04*   (2006.01)
(52) U.S. Cl. ......................................... 433/68; 433/69
(58) Field of Classification Search .................. 433/68, 433/69, 72; 33/513, 514
See application file for complete search history.

(56) References Cited

U.S. PATENT DOCUMENTS

| | | | | | |
|---|---|---|---|---|---|
| 2,286,288 | A | * | 6/1942 | Lover | 433/68 |
| 2,507,118 | A | * | 5/1950 | Opotow | 433/69 |
| 2,587,528 | A | * | 2/1952 | Robinson | 433/69 |
| 2,618,853 | A | * | 11/1952 | Singer et al. | 433/69 |
| 2,840,910 | A | * | 7/1958 | Ford | 433/69 |
| 2,876,541 | A | * | 3/1959 | Jensen | 433/69 |
| 3,066,414 | A | * | 12/1962 | Jarvis | 433/69 |
| 4,932,867 | A | * | 6/1990 | Ueno | 433/69 |

* cited by examiner

*Primary Examiner*—John J Wilson
(74) *Attorney, Agent, or Firm*—Troxell Law Office, PLLC

(57) ABSTRACT

A dental bite configuration recording device comprises an upper base, a lower base, a first biting portion, a second biting portion, and a movable guiding portion. After the user's lower jaw moves to the front, to the left and to the right respectively, these guiding rods of the movable guiding portion will move or slide along the corresponding guiding recessed surfaces of the guiding recessed blocks. And, these recording rods will leave the three-dimensional moving paths on the path recording materials. So, this invention has multiple-positional and three-dimensional bite configuration recording. The guiding recessed blocks are replaceable. And, It will not yield the tongue of the user.

2 Claims, 4 Drawing Sheets

DENTAL BITE CONFIGURATION RECORDING DEVICE

BACKGROUND OF INVENTION

1. Field of the Invention

The present invention relates to a dental bite configuration recording device. Particularly, it is a dental bite configuration recording device that almost can precisely record the actual biting relations. In this invention, it has multiple-positional and three-dimensional bite configuration recording. The guiding recessed blocks are replaceable. And, It will not yield the tongue of the user.

2. Description of the Prior Art

Referring to FIG. 1, the traditional dental bite configuration recording device includes an upper plate 81 and a lower plate 82. The upper plate 81 has a steel pen 811 and several lower fixing hooks 822. The length of steel pen 811 is adjustable. There is a recording plate 821 (for installing a recordable material such as a wax or tin made paper). When the user's upper jaw and the lower jaw are closed, the central position can be fixed and a point 91 will be marked on the recording plate 821 by this steel pen 811, as shown in FIG. 2A. Then, move the user's lower jaw to the front, to the left and to the right respectively. After which, the recording results (including a forward path, left path, and a right path) can be seen in FIG. 2B, FIG. 2C and FIG. 2D. That is also called the gothic arc in the field of dentistry. By doing so, the biting relations about the biting movement can be recorded. Based on the bite configuration, it is possible to produce the denture of this user later.

However, the above-mentioned traditional method has the following disadvantages:

[1] It is a single-positional recording. For the complicated relations about the movement between the upper jaw and lower jaw of the user, it is quite hard to record such complex relations. Consequently, it might be lack of information to produce the denture later.

[2] It is a just plane recording. Because the biting movement is a very complicated three-dimensional movement, it contains the left-right movement, the up-down movement and even the rotational movement. Such single-positional and plane information only can show the horizontal movement. It is impossible to record the actual three-dimensional movement. Therefore, the later proceedings (such as articulator simulation and producing the denture) might be based on a rough prediction or just a baseless estimation. Thus, the possibility is high that the actual biting result of the produced denture will be improper and uncomfortable. For the worst case, the denture has to be abandoned and replaced by a new one.

[3] It will yield the tongue's natural position. Due to the reason that the lower plate 82 will press down the tongue, it will not be a normal and natural biting condition. So, its recording will be different to the recoding under the natural biting condition. Therefore, it is highly possible that the produced denture will be improper and not suitable for the user in the future.

SUMMARY OF THE INVENTION

The primary object of the present invention is to provide a dental bite configuration recording device. It is a multiple-positional and three-dimensional bite configuration recording. It significantly increases the accuracy of dental bite configuration recording. It is very helpful for later proceedings (such as articulator simulation and producing the dentures.).

The second object of the present invention is to provide a dental bite configuration recording device. In which, its guiding recessed blocks are replaceable, so it is suitable for different users (or patients).

The next object of the present invention is to provide a dental bite configuration recording device. It will not yield the tongue of the user. Therefore, the bite configuration can be recorded at the most natural condition. So, its biting relations will be very realistic to the actual one.

In order to achieve above-mentioned objects, a techinical solution is provided. A dental bite configuration recording device comprising:

an upper base;

a lower base;

a first biting portion being substantially U-shaped and stuck on said upper base, said first biting portion having three guiding recesses and a plurality of recording portions, each guiding recess being disposed with a replaceable guiding recessed block, said guiding recessed block having a guiding recessed surface with a central recess thereon; each recording portion containing a path recording material that will be hardened within a predetermined time;

a second biting portion being corresponding to said first biting portion and substantially U-shaped, said second biting portion being stuck on said lower base, said second biting portion having a hollow guiding chamber, a plurality of openings corresponding to said guiding recesses, and a plurality of closed portions corresponding to said recording portion, each closed portion having a recording rod; and a movable guiding portion being movably disposed in said hollow guiding chamber of said second biting portion with a three-dimensional spherical moving range, said movable guiding portion having at least three guiding rods protruding out a predetermined distance over said corresponding openings respectively so as to record three-dimensional moving paths on said corresponding path recording materials;

so as to record a forward path, a left path and a right path on each path recording material by corresponding guiding rods for precisely recording a three-dimensional and multi-positional dental bite configuration.

DETAILED DESCRIPTION OF THE PREFERRED EMBODIMENT

Figure 1:
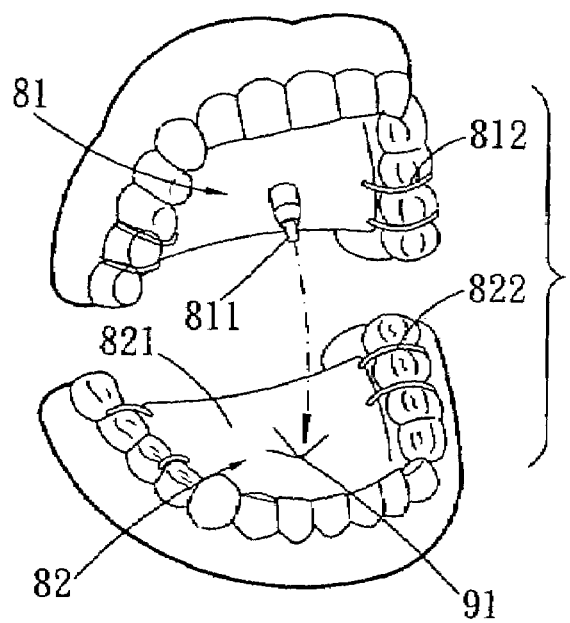
FIG. 1 is a perspective view of the traditional dental bite configuration recording device.
Figure 2A:
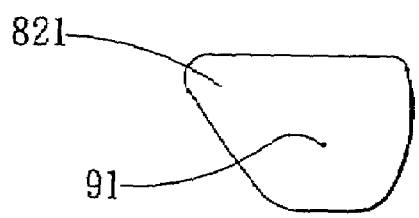
FIGS. 2A, 2B, 2C and 2D are the perspective views showing the related moving paths of the traditional dental bite configuration recording device.
Figure 2B:
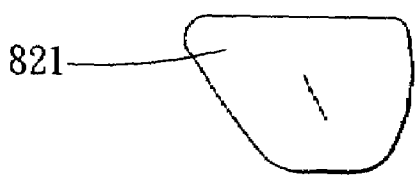
Figure 2C:
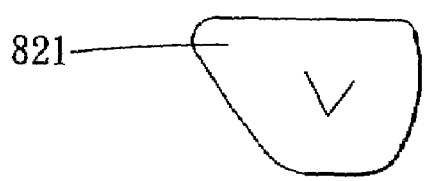
Figure 2D:
Figure 3:
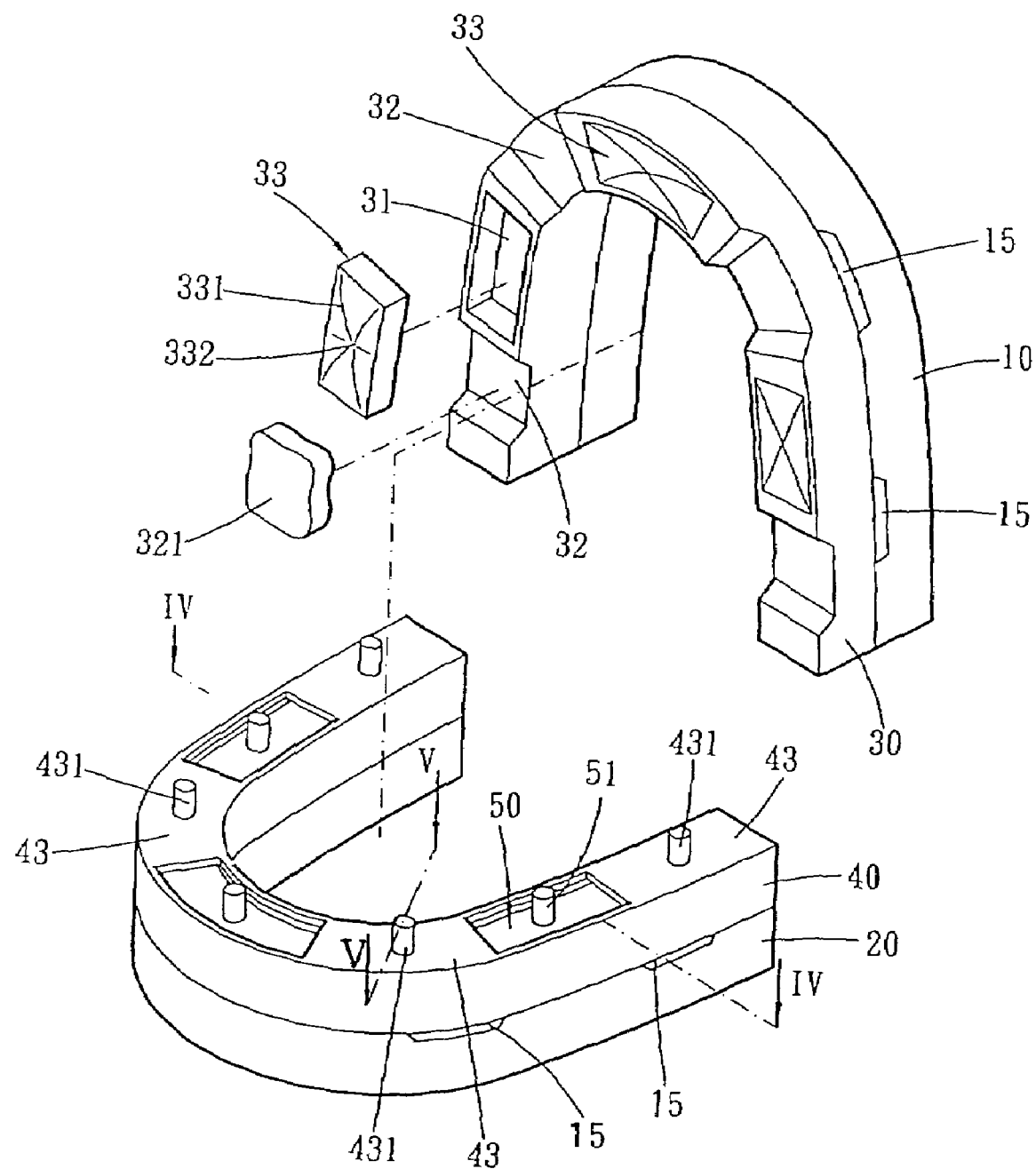
FIG. 3 is a perspective view of the present invention.
Figure 4:
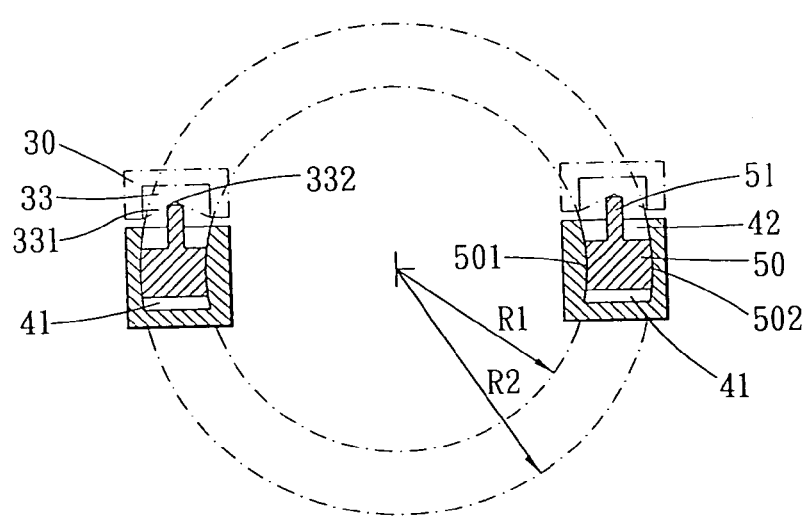
FIG. 4 is a cross-sectional view of a selected portion of this invention.
Figure 5:
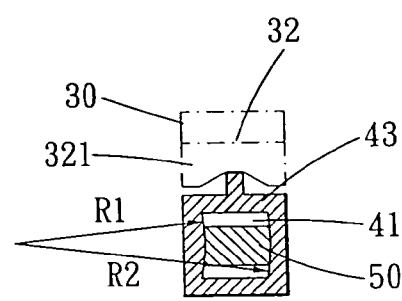
FIG. 5 is another cross-sectional view of a selected portion of this invention.
Figure 6:
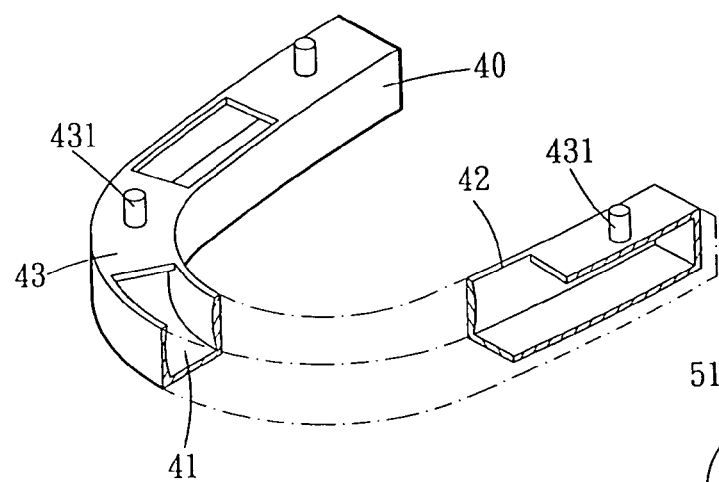
FIG. 6 shows the inner structure of the second biting portion of this invention.
Figure 7:
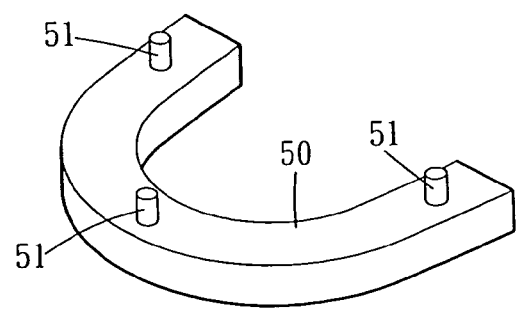
FIG. 7 is a perspective view of the movable guiding portion of this invention.

Referring to FIGS. 3 to 7, the present invention is a dental bite configuration recording device. It mainly comprises an upper base 10, a lower base 20, a first biting portion 30, a second biting portion 40 and a movable guiding portion 50.

The upper base 10 is to secure on the gums around a user's upper jaw's teeth.

The lower base 20 is to secure on the gums around the user's lower jaw's teeth.

About the first biting portion 30, it is substantially U-shaped and can stick on the upper base 10. The first biting portion 30 has at least three guiding recesses 31 and a plurality of recording portions 32. Each guiding recess 31 is disposed with a replaceable guiding recessed block 33. The guiding recessed block 33 has a guiding recessed surface 331 with a central recess 332 thereon. Furthermore, each recording portion 32 contains a path recording material 321 that can be hardened within a short time. For example, it can be a commonly used dental hardening resin (it is a conventional material) so it can stick on the recording portion 32.

Regarding the second biting portion 40, it is corresponding to the first biting portion 30 and is substantially U-shaped, too. This second biting portion 40 is stuck on the lower base 20. The second biting portion 40 has a hollow guiding chamber 41, a plurality of openings 42 corresponding to the guiding recesses 31, and a plurality of closed portions 43 corresponding to the recording portion 32. Furthermore, each closed portion 43 has a recording rod 431.

The movable guiding portion 50 is movably disposed in the hollow guiding chamber 41 of the second biting portion 40 with a three-dimensional spherical moving range. This movable guiding portion 50 has at least three guiding rods 51 protruding out a predetermined distance over the corresponding openings 42 respectively so as to record the three-dimensional moving paths on the corresponding path recording materials 321.

With regard to the spherical rotation, the movable guiding portion 50 has an inner curved surface (which has a first radius R1) and an outer curved surface (which has a second radius R2). The inner and outer curved surfaces 501, 502 have a common spherical center. In addition, from a top view of the movable guiding portion 50, the movable guiding portion 50 extends over half of the circle. For example, it is between ½ and ¾ of the circle. Therefore, when the left part (of the movable guiding portion 50) is pressed down, its right part will move up corresponding. Similarly, if the front part is pressed down, its rear part will move up accordingly.

Therefore, when this invention is installed in a user's mouth and the user's lower jaw moves to the front, to the left and to the right directions respectively, these guiding rods 51 will contact the guiding recessed blocks 33 and move along the guiding recessed surfaces 331. Thus, the present invention can record a forward path, a left path and a right path on each path recording material 321 by the corresponding guiding rods 431. Hence, it can precisely record a three-dimensional and multi-positional dental bite configuration.

In this preferred embodiment, the guiding recessed surface 331 of the guiding recessed blocks 33 has a substantially conical concaved recess. In which, each guiding recessed surface 331 of the guiding recessed block 33 is disposed with a central recess 332 with a sloped surface having a sloped angle between approximately 5 to 35 degrees (or other preset angles).

Of course, the height of the recording rods 431 or the guiding rod 51 can be adjusted (such as by a conventional screw and thread adjusting). Consequently, the best protruding height can be adjusted.

Figure 9:
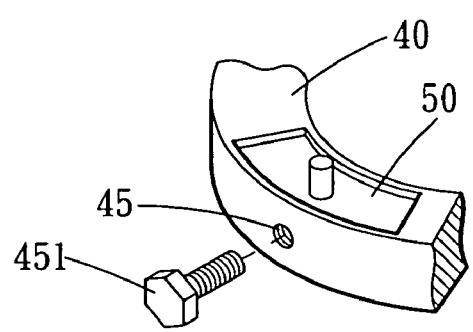
FIG. 9 is a view of the locking element of this invention.

For the actual operation, the example of full artificial dentures is described as follows. First, by using the traditional wax or resin, the upper base 10 and the lower base 20 can be made and temporarily mounted on gums inside the user's mouth. The detailed procedures include:

Step (1): The second biting portion 40 and the movable guiding portion 50 are secured and locked by a locking element 451 (as shown in FIG. 9, such as a screw). Then, put the lower base 20 on the gypsum model. In the ½ or ⅔ area of the rear portion of the gypsum model (measured from the rear molars), a reference point is obtained. Also, there is a front portion (the residual ridge) in this gypsum model. A height about 10 mm to 15 mm is established above the ridge in the front portion. By connecting these two points, a preliminary lower biting plane is obtained. After which, the lower base 20 and the second biting portion 40 are stuck together and are placed inside the user's mouth.

Step (2): Soften the wax 15 (or the resin before hardening). The wax 15 is placed between the upper base 10 and the first biting portion 30. That is, the wax 15 is inside the mouth. The user slightly bites it, so the proper biting height can be determined under an optimal biting engagement. Meanwhile, these guiding rods 51 contact the innermost position (that is the central recess 322) of the guiding recessed blocks 33. At this moment, it is just at the position of centric occlusion (briefly called "CO"). After the wax 15 (or resin) becomes hardened, the upper base 10 and the first biting portion 30 are firmly connected. Then, the locking element 451 can be released.

Step (3): Place the path recording material 321 at the recording portions 32. Then, the user closes one's mouth and then starts a dental bite configuration recording. That is, as shown in FIG. 2, by the use's forward movement, right movement and left movement, the guiding rods 51 will move (or slide) along the guiding recessed surfaces 311. The movable guiding portion 50 will slightly rotate inside the second biting portion 40. These recording rods 431 will leave their three-dimensional moving paths. After repeating this procedure for a period of time, the path recording material 321 will become hardened as a solid one. Thus, it precisely records the actual bite configuration of the user and it is very helpful for later dental proceedings (such as articulator simulation and to produce the dentures).

Figure 8:
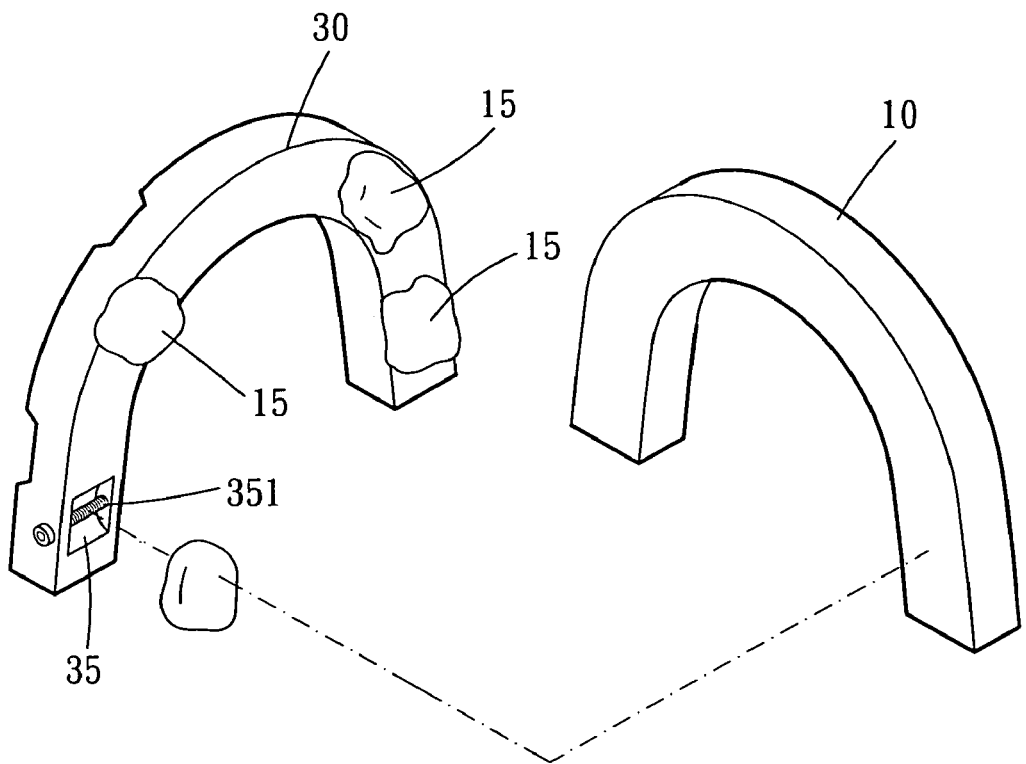
FIG. 8 illustrates the sticking positions of wax.

In addition, referring to FIG. 8, the upper base 10 and the first biting position 30 can be stuck together by fitting several waxes 15 (or resins). The first biting portion 30 also can include a shallow recess 35 and a horizontal stopper 351 (or a bolt). It not only allows the wax 15 fully engage with the horizontal stopper 351, but also makes the wax 15 stick in the shallow recess 35 firmly. Similarly, such shallow recess 35 can be applied to the second biting portion 40 in order to increase its adhering strength and stability.

Moreover, as illustrated in FIG. 9, the front end of the second biting portion 40 is disposed with a locking hole 45 for engaging with the locking element 45. When the locking element 451 is tightened, the entire movable guiding portion 50 is locked.

Besides, if the first biting portion 30 and the second biting portion 40 are changed, it will belong to the equivalent modification of this invention.

Of course, these guiding recessed blocks 33 and these guiding rods 51 can be changed. That is, the guiding recessed blocks 33 are fixed in the movable guiding portions 50, and these guiding rods 51 are fixed on the corresponding guiding recessed 31. Also, it still is another equivalent modification of this invention.

The advantages and functions of this invention can be summarized as follows:

[1] Multiple-positional and three-dimensional bite configuration recording. This invention utilizes the several recording positions (at least three points) and three-dimensional recording way. It significantly increases the accuracy of dental bite configuration recording. It is very helpful for later proceedings (such as articulator simulation and producing the dentures.).

[2] The guiding recessed blocks are replaceable. When the dentist inspects the patient's condition, this dentist can select a suitable guiding recessed blocks with suitable sloped angles (of the guiding recessed surfaces) for later artificial teeth selection (including the consideration of occlusal surfaces). In this invention, the guiding recessed blocks are replaceable, so there are suitable for different users.

[3] It will not yield the tongue of the user. This invention is U-shaped. There is a central space for the tongue of the user. Under such circumstance, the bite configuration can be recorded at the most natural condition. So, its biting relation(s) will be very realistic to the actual one.

The above embodiments are only used to illustrate the present invention, not intended to limit the scope thereof. Many modifications of the above embodiments can be made without departing from the spirit of the present invention.

What is claimed is:

1. A dental bite configuration recording device comprising:
   an upper base;
   a lower base;
   a first biting portion being substantially U-shaped and stuck on said upper base said first biting portion having three guiding recesses and a plurality of recording portions, each guiding recess being disposed with a replaceable guiding recessed block, said guiding recessed block having a guiding recessed surface with a central recess thereon; each recording portion containing a path recording material that will be hardened within a predetermined time;

a second biting portion corresponding to said first biting portion and substantially U-shaped, said second biting portion being stuck on said lower base, said second biting portion having a hollow guiding chamber, a plurality of openings corresponding to said guiding recesses, and a plurality of closed portions corresponding to said recording portion, each closed portion having a recording rod; and a movable guiding portion being movably disposed in said hollow guiding chamber of said second biting portion with a three-dimensional spherical moving range, said movable guiding portion having at least three guiding rods protruding out a predetermined distance over said corresponding openings respectively so as to record three-dimensional moving paths on said corresponding path recording materials;

so as to record a forward path, a left path and a right path on each path recording material by corresponding guiding rods for precisely recording a three-dimensional and multi-positional dental bite configuration.

2. The dental bite configuration recording device as claimed in claim 1, wherein said central recess of each guiding recessed surface of the guiding recessed block having a sloped surface with a sloped angle between approximately 5 to 35 degrees.

* * * * *